United States Patent [19]
Angel et al.

[11] Patent Number: 6,159,144
[45] Date of Patent: Dec. 12, 2000

[54] RADIOACTIVE SUBSTANCE ADMINISTRATOR

[76] Inventors: Jeff Angel, 901 Hillcrest Dr., Bldg. 19, Apt. 606, Hollywood, Fla. 33021; David York, 302 Terry La., Caryville, Tenn. 37714

[21] Appl. No.: 09/265,014

[22] Filed: Mar. 9, 1999

[51] Int. Cl.$^7$ ....................................... A61N 5/00
[52] U.S. Cl. ................... 600/5; 604/263; 604/535
[58] Field of Search ..................... 604/162, 263, 604/218, 535; 600/1–6, 436, 432

[56] References Cited

U.S. PATENT DOCUMENTS

| | | |
|---|---|---|
| 3,973,554 | 8/1976 | Tipton . |
| 4,471,765 | 9/1984 | Strauss et al. . |
| 5,514,071 | 5/1996 | Sielaff, Jr. et al. ..................... 600/3 |
| 5,961,439 | 10/1999 | Chernomorsky et al. ............... 600/4 |

Primary Examiner—Mark Bockelman
Attorney, Agent, or Firm—Malloy & Malloy, P.A.

[57] ABSTRACT

A radioactive substance administrator including a syringe structured to receive a dosage of the radioactive substance therein; a containment housing structured to contain the syringe and including a radioactivity retardant material, structured to substantially attenuate the emergence of radioactivity through the containment housing, and a plunger track structured to contain a plunger assembly of the syringe movably therein; an exterior actuation assembly operatively associated with the containment housing and structured to actuate the plunger assembly of the syringe; and a secondary shielding assembly operatively associated with an outlet of the containment housing and structured to permit the passage of the radioactive substance to the patient while also attenuating radioactivity emerging from the outlet of the containment housing and radioactivity emanating from the radioactive substance exiting the containment housing.

28 Claims, 3 Drawing Sheets

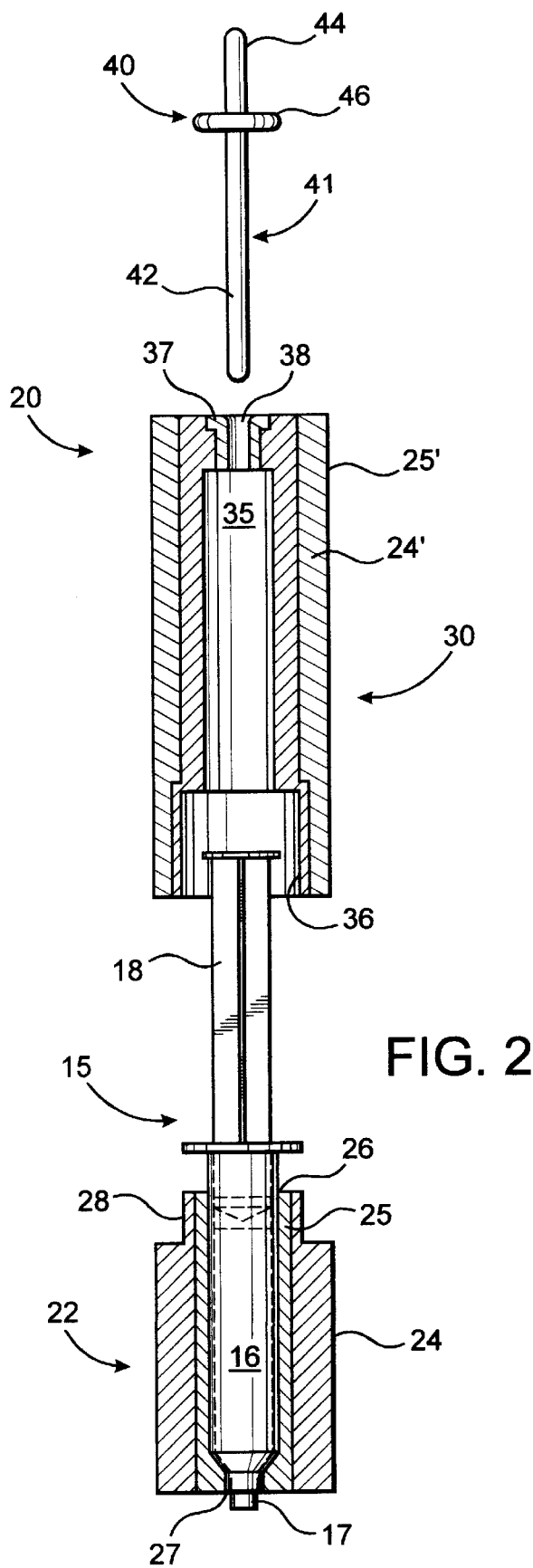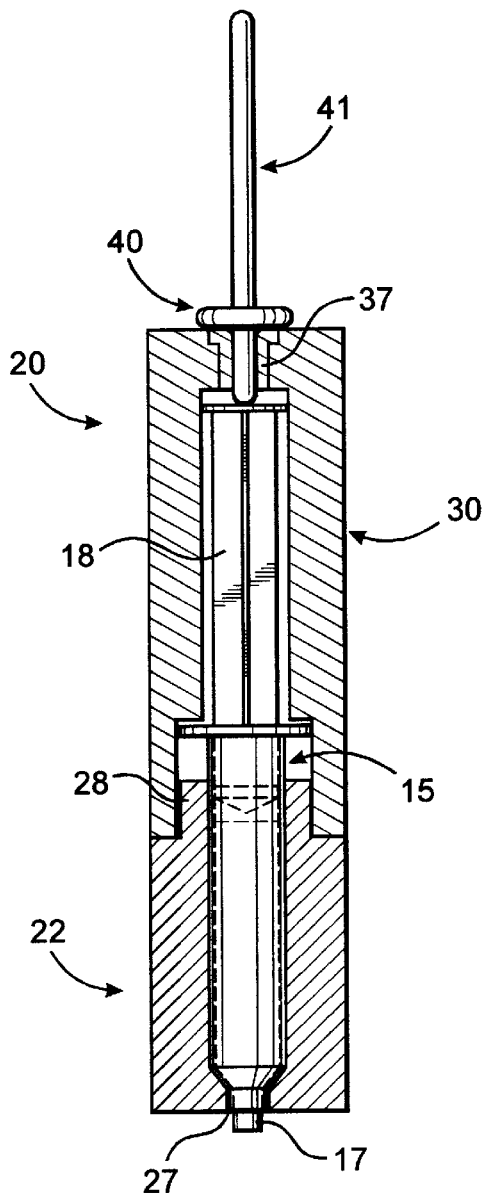
FIG. 2
FIG. 5

RADIOACTIVE SUBSTANCE ADMINISTRATOR

BACKGROUND OF THE INVENTION

1. Field of the Invention

The present invention relates to a radioactive substance administrator utilized to safely administer a radioactive or radiation emitting substance, such as a radionuclide to a patient during the performance of various procedures, the administrator being structured to be convenient to utilize, implement and manipulate, and to substantially shield a user thereof from excessive exposure to a radioactive material, thereby minimizing long term exposure to individuals who regularly work with the radioactive substances.

2. Description of the Related Art

The administration of radionuclides to diagnose and treat various diseases is a well established science. Virtually every hospital in the United States, as well as many in foreign countries, have a nuclear medicine department dedicated to localizing and/or treating a myriad of pathologies utilizing radionuclides as part of an examination procedure. In particular, each of the many patients who undergoes a radionuclide exam is administered a radionuclide, either orally, intravenously, intracavitarily, or subcutaneously for an affected area. Once within the patient, the radionuclide, in combination with a variety of other testing equipment responsive thereto, provides valuable feed back as to the condition of the patient or the location of a particular source of problems.

By far the most common type of administration of the radionuclide is intravenous administration. Specifically, intravenous administration of the radionuclide involves the injection of the radionuclide into a patient, typically through an intravenous type tube. Often, however, the radionuclide is not directly introduced into the patient, such as by direct penetration of a loaded syringe, but rather in the many cases the radionuclide is introduced in line with an intravenous tube or connection that is otherwise coupled to the patient, and utilizing an acceptable intravenous fluid the radionuclide material is pushed or washed into the patient's blood stream. The travel of the radionuclide through the patient's blood stream can therefore be subsequently monitored due to its radioactivity emitting properties.

As a result of the popular nature and frequent utilization of intravenous administration of radionuclides, intravenous radionuclide administration is a primary source of exposure to radiation for medical operators. In particular, although a variety of different techniques are currently employed in an effort to minimize the exposure of any individual, including the patient and medical operator, to radioactive substances, for the medical operator this risk is greatly increased due to the large volume of procedures which they must perform each and every day. For example, although the amount of radioactivity experienced by a particular patient during a particular procedure may be relatively insignificant, repeated daily exposure to even minimal amounts of radioactivity on a recurrent basis can eventually lead to prolonged, adverse reactions in the medical operator equivalent to a high single exposure. Accordingly, any structure or assembly which further minimizes the exposure of the medical operators to radioactivity, will decrease the overall exposure of those individuals over a prolonged period of time by drastic amounts.

As indicated, presently in the art the most common type of administration of radionuclide and/or other radioactive substances which may be used for similar testing, is the intravenous injection of the radionuclide. Prior to use, the radioactive substance is typically contained within a shielded container, which in turn is usually contained within a shielding working area. When administration of a dosage is required, a medical operator manipulates the necessary equipment and substances within the shielded environment so as to dispense an appropriate amount of the radioactive substance into a typically conventional type syringe. At this stage, because of the shielded working area, the medical operator as well as any other individuals present in the vicinity of the radioactive substance are fully shielded and protected from radioactive emissions. Unfortunately, however, once the dosage has been dispensed into the syringe, the medical operator must eventually remove the loaded syringe from the shielded working area in order to effectively administer the contents of the syringe to the patient. It is during this time period that a majority of the exposure to the radioactive substance is experienced, and as a result, it is during this time period which the attenuation of the radioactivity would be most beneficial.

Presently in the art there have been numerous attempts to develop shielding type structures which will somewhat shield the syringe during transport and administration of the radioactive substance to the patient. Unfortunately, however, most such radiation shields, which typically fit only over the main body of the syringe, do not substantially shield the entire syringe from the emergence of radioactivity. In particular, because the plunger type assembly of the syringe must be depressed by the medical operator in order to effectuate proper administration, the plunger portions are usually open and fully exposed to unhampered radioactivity emission. Naturally, this can be particularly hazardous when a medical operator stands over a syringe and/or places their hand over the unshielded rear of the syringe during dispensing. Indeed, it is noted that the radioactivity is directed outwardly from unshielded portions of a syringe much like a beam.

Of additional concern is the open dispensing end of the syringe and the area immediately outside the syringe during administration. As can be appreciated, the open dispensing end of the syringe must typically be completely open so as to provide for the injection of the radioactive substance. As a result, even though a medical operator can take great care in ensuring that the open end is not "pointed" at themselves or other individual, when the dispensing actually takes place in the vicinity of the patient, the inconsistent manipulation that can often take place, including the putting down of the dispensing syringe so as to actuate an intravenous fluid source or open a valve, can sometimes result in excessive dispersement of radioactivity. Even more so, utilizing the conventional techniques for the intravenous injection of the radioactive substance, the radioactive material is typically ejected from the syringe into a conduit until the intravenous fluid source pushes the radioactive substance into the patient. As can be appreciated, even during substantially rapid manipulation, the radioactive substance will necessarily be maintained completely exposed for a certain period of time before the intravenous fluid can rapidly push it into the patient. As a result, it is seen that there is a substantial need in the art for a radioactive substance administrator which will effectively maintain the radioactive substance shielded to the maximum extent possible for as much time as is possible during which exposure may be prevalent. Furthermore, such an administrator should be easy to manipulate without requiring excessive adaptation or modification of existing dispensing syringe type structures. For example, presently in the art large self contained dispensing carts including elaborate and very heavy shielded mechanical structures are in existence for the dispensing of radioactive material. Such devices, however, while attempting to completely maintain shielding of the radioactive substance from the medical operator, still require the medical operator to effectively introduce the radioactive substance into the dispensing device, and require the expensive, heavy and complex device be handled and manipulated into a dispensing position. Naturally, such devices can often be substantially impractical for extensive and repeated uses, especially in circumstances where multiple tests utilizing radioactive substances are being undertaking at one time. Accordingly, a preferred radioactive substances administrator should not only be substantially safe by significantly shielding radioactive emission, but should not go to an opposite extreme by being overly costly, complex and/or cumbersome so as to compromise the general usability of the system by trained medical operators.

SUMMARY OF THE INVENTION

The present invention relates to a radioactive substance administrator. In particular, the administrator of the present invention is structured to provide for the effective and safe administration of a radioactive substance, such as a radionuclide, to a patient, and preferably into a patient, such as intravenously.

Included as part of the radioactive substances administrator of the present invention is a syringe. The syringe is structured to receive a dosage of the radioactive substance therein. Furthermore, the syringe includes a dispensing end from which the radioactive substance exits the syringe, and a plunger assembly used to urge the radioactive substance through the dispensing end.

The radioactive substance administrator of the present invention further includes a containment housing. The containment housing removably contains the syringe in a substantially comprehensive manner. Moreover, the containment housing includes at least a radioactivity retardant material layer therein. The radioactivity retardant material layer is structured and disposed to substantially enclosed the syringe containing the radioactive substance, and is thereby structured to substantially attenuate the emergence of radioactivity through the containment housing.

Defined within the containment housing is a plunger track. In particular, the plunger track is defined and structured to contain the plunger assembly of the syringe through its full range of motion relative to the body of the syringe. As a result, the plunger assembly is able to effectively move in order to at least partially urge the radioactive substance out of the syringe through the dispensing end. Furthermore, an exterior actuation assembly is provided so as to allow the direct manipulation and actuation of the plunger assembly, while still maintaining the plunger assembly contained within the containment housing.

The containment housing of the present invention further includes an outlet defined therein. The outlet is cooperatively associated with the dispensing end of the syringe and is structured to permit passage of the radioactive substance out of the containment housing for subsequent administration to the patient. Furthermore, the outlet is preferably configured to substantially conform to the dispensing end of the syringe so as to provide minimal emergence of radioactivity from the front end of the containment housing during use. Operatively associated with the outlet of the containment housing, however, is a secondary shielding assembly. In particular, the secondary shielding assembly permits the passage of the radioactive substance to the patient while also attenuating radioactivity from the outlet of the containment housing during the dispensing to the patient. Specifically, the secondary shielding assembly is structured to substantially shield and attenuate radioactivity that emerges from the radioactive substance itself as it exits the containment housing and is no longer principally shielded by the containment housing. Accordingly, only a small amount of radioactivity is emitted prior to introduction of the radioactive substance into the patient.

It is an object of the present invention to provide a radioactive substance administrator which is convenient and effective to manipulate by a medical operator, yet which provides substantially increased safety and protection against radioactivity emissions.

A further object to the present invention is to provide a radioactive substance administrator which utilizes a medical operator's experience by permitting the medical operator to maintain control over the administration process, including control over the quantities of radioactive substance administered and the rate of administration, but which also substantially increases the safe use of radioactive substances by further minimizing exposure by the medical operator to radioactive emissions.

Yet another object to the present invention is to provide a radioactive substance administrator which substantially shields and attenuates radioactivity emissions from a radioactive substance, even subsequent to emergence of the radioactive substance from a protective syringe as it is being prepared for introduction into a patient.

An added object to the present invention is to provide a radioactive substance administrator which is substantially convenient to manipulate in a uniform and consistently safe manner without having to put down or release radioactive components from secured control in order to manipulate other administration components.

Also an object of the present invention is to provide a radioactive substance administrator which is substantially cost effective to produce and is significantly durable over an extended period of time and after repeated uses.

An added object of the present invention is to provide a radioactive substance administrator which is substantially easy to implement and manipulate.

BRIEF DESCRIPTION OF THE DRAWINGS

For a fuller understanding of the nature of the present invention, reference should be had to the following detailed description taken in connection with the accompanying drawings in which:

FIG. 2 is an exploded cross section view of the syringe and the containment housing of the radioactive substance administrator of the present invention;

FIG. 5 is a cross section view of the syringe operatively disposed in an assembled and shielding containment housing.

Like reference numerals refer to like parts throughout the several views of the drawings.

DETAILED DESCRIPTION OF THE PREFERRED EMBODIMENT

Figure 1:
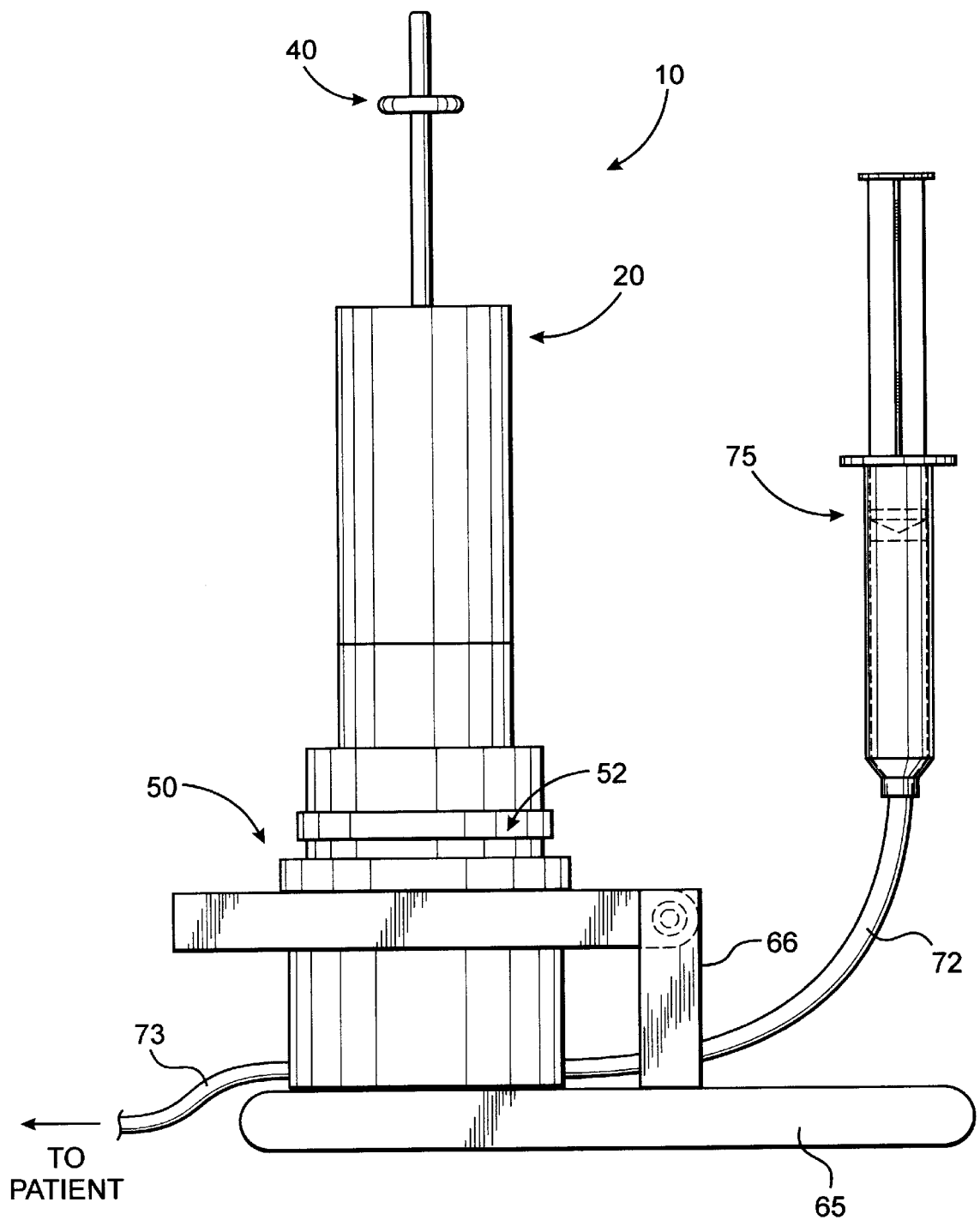
FIG. 1 is a side view of the radioactive substance administrator of the present invention in use.

As shown throughout the Figures, the present invention is directed towards a radioactive substance administrator, generally indicated as 10. In particular, the radioactive substance administrator 10 is to be utilized to dispense and administer a radioactive substance, such as a radionuclide, to a patient in a variety of medical applications, and especially for diagnostic type applications. Specifically, in the diagnostic type applications a radionuclide is typically injected into a patient such that the movement of the radionuclide through the patient can be monitored by external devices. While the extent of the radioactivity emitted by the radioactive substance during each administration is typically relatively small and will generally not excessively harm a particular patient, the frequency with which the tests are performed by hospital practitioners and the medical operators leads to repeated exposure to the radioactivity, and accordingly, an increased potential risk of prolonged overexposure. To this end, the radioactive substance administrator 10 of the present invention provides for the effective and convenient administration of the radioactive substance to the patient in a substantially easy to manipulate and cost effective manner, while maximizing the radioactivity attenuation relative to the medical operator, thereby minimizing the overall exposure to be experienced over the course of a large number of procedures.

Looking specifically to the radioactive substance administrator 10 of the present invention, it includes a syringe, generally 15. The syringe 15 can be of a variety of operable configurations, and can be formed of a relatively inexpensive and preferably disposable material such as a plastic material. As a result, the syringe 15, after a single use can be effectively disposed of to avoid contamination. Of course, as the syringe 15 is never placed in direct contact with a patient, a partially or completely re-useable syringe may hypothetically be employed, however, disposability is generally preferred in the medical field. The preferred syringe 15 includes a main compartment 16 in which a dosage of the radioactive substance to be administered is contained. Furthermore, the syringe 15 includes a plunger assembly 18 which preferably moves within the main compartment 16 so as to draw in and urge out the dosage from the main compartment 16. To this end, the syringe 15 includes a dispensing end 17 through which the radioactive substance will pass into and out of the main compartment 16 of the syringe 15. In particular, whether or not a hypodermic needle is connected at the dispensing end 17, the dispensing end 17 of the syringe 15 is disposed in fluid flow communication with the material to be administered. Preferably by drawing on the plunger assembly 18, a vacuum is generated and the material to be administered, in the present case the radioactive substance, is drawn into the main compartment 16 of the syringe 15 such that the appropriate dosage can be measured, such as by indicia on the syringe 15 or more commonly by a dose calibration device. Subsequently, the plunger assembly 18 is depressed and pushed into the main compartment 16, thereby urging the dosage that has been contained within the main compartment 16 out through the dispensing end 17 for appropriate delivery to a patient.

The radioactive substance administrator 10 of the present invention further includes a containment housing, generally indicated as 20 and comprising a retention portion 22 and a track portion 30. The containment housing 20 is structured to substantially and removably contain the syringe 15, preferably after it has been loaded with a dosage of the radioactive substance. In particular, in use the radioactive substance is typically drawn into the syringe 15 at a shielded area. Subsequently, the syringe 15 is introduced into the containment housing 20, after which it may be conveniently and effectively manipulated for subsequent dispensing of a dosage to the patient. In this way, the relatively inexpensive syringe 15 can be disposed of after each use, while the containment housing 20 can be re-used, as it is preferably only structured to removably contain the syringe 15 during time periods when it is not disposed within a shielded area and contains the radioactive substance. Of course, it is noted that the syringe structure could be integrally formed with the containment housing, including the use of a single, shielded combination syringe and containment housing.

Looking in further detail to the containment housing 20, it is preferably constructed at least in part of a radioactivity retardant material layer 25 so as to significantly attenuate the emergence of radioactivity through the containment housing 20. Specifically, while the entire containment housing 20 may be formed of the radioactivity retardant material such that the entire body of the containment housing 20 defines the radioactivity retardant material layer, in the preferred embodiment a substantially non malleable, rigid exterior layer 24 is preferably provided to supportively enclose the radioactivity material layer 25. In particular, the preferred embodiment of the present invention preferably utilizes a leaded material as the radioactivity retardant material due to its beneficial radioactivity attenuating properties. Unfortunately, however, a material such as lead is substantially malleable and after an extended, repeated period of use can become worn or deformed so as to diminish it ability to attenuate radioactivity, such as through thinner areas, cracks and/or creases, and/or so as to provide an imprecise fit between the syringe 15 in a containment housing 20. As such, a material, such as steel or another rigid metal, is utilized to define a substantial non-malleable rigid exterior layer 24, thereby ensuring that the containment housing 20 substantially retains it shape and maintains the precise engagement with a secondary shielding assembly 50, to be described in greater detail subsequently, after repeated uses. As to the radioactivity retardant material layer, it is understood that it can define an entire interior layer, as illustrated in the preferred embodiment of the Figures, or may be interposed between multiple material layers, including rigid walls and/or interior padding layers and/or other types of materials as may be deemed appropriate, so long as the radioactivity retardant material layer is contained wthin the containment housing 20 and generally encases and surrounds the syringe 15 once it is disposed within the containment housing 20. Also, multiple layers of the radioactivity retardant material can be used, including multi-particle layers, composites or mixtures of the radioactivity retardant material with other materials. Further, as other structures and devices are developed to shield or attenuate the emergence of radioactivity, those may also be incorporated to define the contemplated radioactivity retardant material layer of the present invention.

The containment housing 20 generally includes the retention portion 22 and the track portion 30. Specifically, the retention portion 22 is structured to enclose and contain the main compartment 16 of the syringe 15 therein. Conversely, the track portion 30 is structured to include a plunger track 35 defined therein. The plunger track 35 is structured and disposed to permit the preferred reciprocating movement of the plunger assembly 18 of the syringe 15 relative to the main compartment 16 of the syringe 15, thereby effectively providing for the urging of the radioactive substance out from the dispensing end 17 of the syringe 15. The track portion 30, as it is also a part of the containment housing 20, also includes the preferred radioactivity retardant material layer 25' and the preferred substantially non-malleable rigid exterior layer 24' so as to define it shape. The track portion 30 and the retention portion 22 are, however, preferably structured to be removably coupled with one another so as to facilitate the removable positioning of the syringe 15 in a secured and shielded fashion therein. In the preferred embodiment, the retention portion 22 includes an introduction opening 26 into which the main compartment 16 of the syringe 15 is introduced for containment by the retention portion 22. Defining the opening 26 is a hub structure 28, which in the preferred embodiment includes a male hub portion. Conversely, the track portion 30 includes a hub section 36, correspondingly a female hub portion in the preferred embodiment, which is structured to mate with the hub structure 28 on the retention portion 22, thereby providing a generally secured, closed retaining engagement between the retention portion 22 and the track portion 30. Moreover, as illustrated by the Figures, the radioactivity retardant material layer 25, 25', although not absolutely required, preferably overlaps through the hubs 28 and 36 so as to ensure that the syringe 15 is substantially shielded against radioactivity emissions from about the periphery of the containment housing 20.

In the preferred embodiment, the radioactive substance administrator 10 of the present invention also preferably includes a secondary shielding assembly, generally 50. Specifically, the secondary shielding assembly 50 is structured to be operatively associated with the containment housing 20 in such a manner as to permit passage of the radioactive substance to the patient, while also further attenuating radioactivity emerging from the radioactive substance and the containment housing 20 during actual dispensing of the radioactive substance and its emergence from the dispensing end 17 of the syringe 15.

In the preferred embodiment, the secondary shielding assembly 50 includes primarily a main shielding body 52. The main shielding body 52 is constructed at least in part of a radioactivity retardant material and is structured to receive an end of the containment housing 20 which includes an outlet 27 defined therein. In particular, the containment housing 20 preferably includes an outlet 27 wherethrough the radioactive substance is urged through the dispensing end 17 of the syringe 15 and exits the containment housing 20. This outlet 27 is sized and fitted to substantially correspond to the dispensing end 17 of the syringe 15, thereby minimizing radioactivity emissions therethrough, such as during transport of the containment housing 20 with a loaded syringe 15 therein from another shielded location to the site of administration.

The main shielding body 52 includes a generally open interior chamber 54 into which the containment housing 20 is introduced. As illustrated in FIG. 1, the containment housing 20 is preferably, but not necessarily, only partially introduced into the main shielding body 52 of the secondary shielding assembly 50 such that the outlet 27 of the containment housing 20 is disposed generally within the interior chamber 54 of the main shielding body 52. As a result, a radioactivity retardant material layer 55 which is preferably included to further define the main shielding body 52, further attenuates the emergence of radioactivity from the outlet 27 of the containment housing 20. Furthermore, a clamp structure 60 is preferably included, either separately but preferably as an integral part of the main shielding body 52. The clamping structure 60, such as through a tightening screw 62 is structured to clampingly secure the main shielding body 52 about the containment housing 20, thereby ensuring a snug and secure fit therebetween, and ensuring that no radioactivity will generally emerge from therebetween. Indeed, it is for this reason that the preferred structure wherein a steel, rigid exterior layer 24 is provided, such that after repeated uses and repeated clamping by the clamping structure 60 the containment housing 20 does not become deformed resulting in imprecise engagement between the containment housing 20 and the secondary shielding assembly 50 and in radioactivity "leaks" therebetween.

Operatively coupled with the dispensing end 17 of the syringe 15, preferably through the outlet 27 of the containment housing 20, is a connector hub 70. The connector hub 70, which may be integral with one or more other components of the present invention is preferably defined by a separate three way connector with two one way valves wherein one inlet is coupled with the dispensing end 17 of the syringe 15. Preferably, but not necessarily, the connector hub 70 is disposed within the interior chamber 54 of the main shielding body 52 during dispensing of the radioactive substance. Additionally, the connector hub 70 is also preferably operatively coupled with an intravenous fluid source 75, such as a secondary syringe. The intravenous fluid source 75 is structured to contain a quantity of an intravenous fluid which essentially pushes or washes the radioactive substance into the patient. As a result, an outlet of the connector hub 70 is typically connected intravenously to the patient. In practice, it is seen that a practitioner first urges the radioactive substance from the syringe 15 through the connector hub 70. That radioactive substance is then generally maintained in line within an elongated administration conduit 73 such that a subsequent administration of the intravenous fluid from the intravenous fluid source 75 will serve to urge the radioactive substance through the administration conduit 73 to the patient. Based upon the structure of the present invention, and in particular the engagement between the containment housing 20 and the secondary shielding assembly 50, after the radioactive substance exits the syringe and is waiting to be urged into the patient, the radioactive substance may be at least partially shielded so as to reduce the radioactivity that will emerge therefrom. Also, it is noted that due to the inclusion of the preferred two one way valves, the intravenous fluid is generally prevented from being inadvertently urged up into the syringe 15 containing the radioactive substance. However, such construction of the connector hub 70 either to automatically allow two inlets and only one outlet with alternative actuatable configurations can be easily provided.

Figure 3:
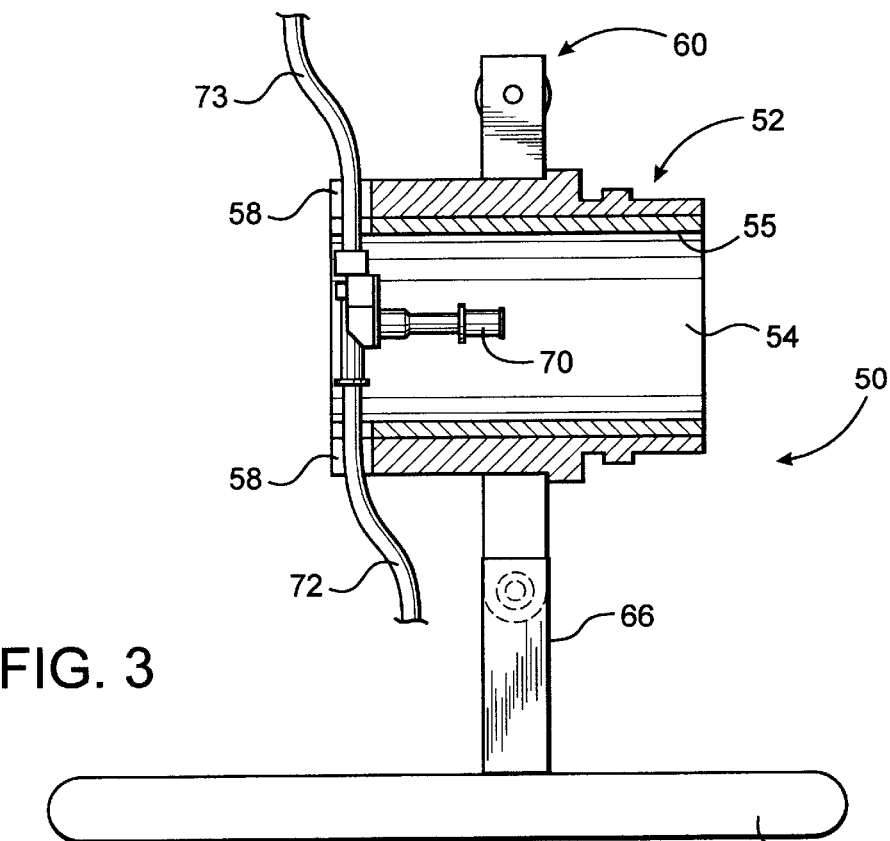
FIG. 3 is a side cross section view of the secondary shielding assembly of the radioactive substance administrator of the present invention.
Figure 4:
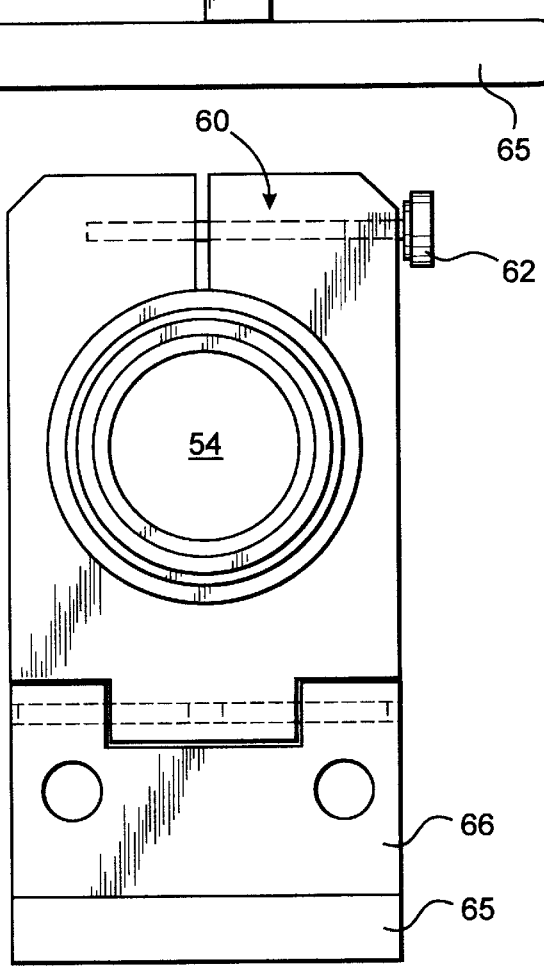
FIG. 4 is a side plan view of the secondary shielding assembly of the radioactive substance administrator of the present invention.

Looking further to the secondary shielding assembly 50 and in particular the main shielding body 52, although structure may be provided to include an open bottom for passage of the elongated administration conduit 73 and a preferred elongate intravenous fluid conduit 72 connected with the intravenous fluid source 75, in another illustrated embodiment the main shielding body 52 includes at least two apertures 57 and 58 defined therein. In particular, the apertures 57 and 58 may be wholly defined through the surrounding wall structure of the main shielding body 52, or, as illustrated in the embodiment of FIGS. 1 and 3, may be defined in a lowermost portion of the main shielding body 52 so as to only partially encircle the conduit passing therethrough. The second embodiment of the apertures 57 and 58 is preferred because of the preferred configuration wherein the main shielding body 52 is preferably pivotally connected to a base 65. Specifically, as illustrated in the Figures, the main shielding body 52 is preferably structured to be normally disposed in a generally horizontal orientation, as in FIG. 3. Such positioning of the main shielding body 52 facilitates introduction of the containment housing 20 in a rapid and efficient manner which minimizes possible adverse effects of emissions of the radioactivity through the outlet 27 of the containment housing 20. Once the containment housing 20 has been effectively positioned and secured in the main shielding body 52, however, the main shielding body 52 with the containment housing 20 secured therein is preferably pivoted on a support stanchion 66 into a generally vertical orientation, as in FIG. 1. In this generally vertical orientation, radioactivity emerging from the outlet 27 of the containment housing 20 is generally directed towards the base 65 and is further substantially attenuated, especially since the base 65 is preferably constructed at least in part from a radioactivity attenuating material. In this regard, it is noted that some spacing may be provided between the vertical orientation of the main shielding body 52 and the base 65, with the connector hub 70 generally protruding from the main shielding body 52, however, in the illustrated preferred embodiment a generally abutting engagement is provided so as to minimize the escape of radioactivity therebetween. Indeed, if desired the apertures 57 and 58 may include angular or right angle configurations within the exterior wall structure of the main shielding body 52 so as to further block the escape of radioactivity from the main shielding body 52 unless directly along the administration conduit 73. Such a configuration may be particularly beneficial as a sufficient length of the administration conduit 73 will preferably be maintained within the main shielding body 52 until the intravenous fluid washes it therethrough to the patient. In this manner even while a hospital practitioner is manipulating between one actuation assembly and another, the radioactive substance is generally maintained in a shielded position until a more rapid, immediate administration through the administration conduit 73 directly into the patient is achieved. In another, alternative embodiment, the main shielding body 52 may include an enclosed and radioactivity shielded bottom surface so as to eliminate the preferred requirement of the shielding base 65 being in close proximity to the vertically oriented main shielding body 52.

As indicated from the preceding, the syringe 15 of the present invention is preferably initially utilized at a shielded location so as to dispense a required dosage of the radioactive substance. Subsequently, the main compartment 16 of the syringe 15 is introduced into the retention portion 22 of the containment housing 20, and is enclosed by a track portion 30 of the containment housing 20. Typically, this containment of the syringe 15 includes the plunger assembly 18 of the syringe 15 disposed in an extended position, as illustrated in FIG. 2, so as to be ready for subsequent depression in order to urge the radioactive substance from the dispensing end 17 of the syringe 15. As a result, the track portion 30 includes the generally elongate plunger track 35 to provide for effective containment of the entire syringe 15 even when the plunger assembly 18 of the syringe 15 is at generally a maximum extended position. Naturally, this plunger track 35 also permits the effective pushed movement of the plunger assembly 18 once administration of the radioactive substance is required. Specifically, once the loaded syringe 15 is contained within the containment housing 20, a medical operator can then generally remove the containment housing 20 from the shielded location and easily manipulate the containment housing 20 to a proximity of the patient for subsequent administration. In this regard, the containment housing 20 is introduced into the main shielding body 52 of the secondary shielding assembly 50 and is clamped into a generally secured configuration subsequent to operative coupling of the connector hub 70 with the dispensing end 17 of the syringe 15. Of course, it is noted that the connector hub 70 may also be coupled with the outlet 27 of the containment housing 20 so as to provide for increased shielding, however, it is preferred that direct coupling between the connector hub 70 and the dispensing end 17 of the syringe 15 be provided so as to effectively achieve disposal of the syringe 15 and the connector hub 70 subsequent to a particular use. Once the containment housing 20 is clamped into the main shielding body 52 of the secondary shielding assembly 50, the main shielding body 52 is preferably pivoted into its generally vertical orientation, thereby generally vertically orienting the syringe 15 and the plunger assembly 18.

In order to provide for effective actuation of the plunger assembly 18 without having to leave the plunger assembly 18 substantially exposed and non-shielded, the radioactive substance administrator 10 of the present invention further includes an exterior actuation assembly, generally indicated as 40. In particular, the track portion 30 of the containment housing 20 preferably includes a plunger port 38 defined therein and preferably precisely configured by a shielded hub 37. The plunger port 38 is structured to provide exterior access from the exterior actuation assembly 40 into the plunger track 35 for appropriate actuation of the plunger assembly 18. In the preferred embodiment, the exterior actuation assembly 40 includes an elongate segment 41. This elongate segment 41 preferably includes a substantially rigid configuration, and may be formed in part of a shielding and/or attenuating material if desired. As seen in FIG. 2, the elongate segment 41 of the exterior actuation assembly 40 preferably includes an actuation end 42 and a safety end 44 defined relative to one another by a stopper assembly 46. Looking first to the actuation end 42, it is preferably substantially elongate and is structured to be introduced through the plunger port 38 and into the plunger track 35 of the containment housing 20. Furthermore, the actuation end 42 of the exterior actuation assembly 40 is substantially elongate so as to provide for effective pushing of the plunger assembly 18 a required amount to urge at least a majority of the radioactive substance from the syringe 15. As a result, only the plunger port 38 itself remains open on the track portion 30 of the containment housing 20 as a potential source for the emission of radioactivity. Additionally, so as to further attenuate any radioactivity which may emerge through the plunger port 38, the stopper 46 is preferably provided entirely of or is filled with a radioactivity attenuating material. As a result, radioactivity emerging through the plunger port 38 will be typically shielded by the stopper assembly 46, especially as the medical operator's finger gets closer and closer to the plunger port 38 during inward pushing of the actuation end 42 of the exterior actuation assembly 40. Indeed, such a configuration is particularly beneficial as the medical operator can generally maintain a normal "feel" over the administration, and can utilize their experience accordingly. Conversely, and as illustrated on the Figures, the safety end 44 of the exterior actuation assembly 40 is relatively short as compared with the actuation end 42. In particular, the safety end 44 is structured to be introduced into the plunger port 38 during transport of the containment housing from a shielding location to the secondary shielding assembly 50. As a result, the safety end 44 is not sufficiently elongate so as to depress the plunger assembly 18 and cause dispensing of the radioactive substance, however, it is sufficient so as to maintain the stopper assembly 46 in generally proximate abutting engagement with the containment housing 20 so as to effectively shield the emergence of radioactivity through the plunger port 38. Accordingly, maximum shielding is maintained at all times, yet effective and convenient manipulation by a medical operator can be achieved, including manual administration of the radioactive substance from the syringe 15 in a rapid and transportable manner.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,
What is claimed is:

1. To administer a radioactive substance to a patient, a radioactive substance administrator comprising:

a syringe structured to receive a dosage of the radioactive substance therein;

said syringe including a dispensing end from which the radioactive substance exits said syringe, and a plunger assembly structured to urge the radioactive substance through said dispensing end;

a containment housing structured to substantially and removably contain said syringe, said containment housing including at least a radioactivity retardant material layer disposed in substantially enclosing relation about said syringe and structured to substantially attenuate the emergence of radioactivity through said containment housing;

said containment housing including a plunger track defined therein and structured to contain said plunger assembly of said syringe, while also permitting movement of the plunger assembly so as to at least partially urge the radioactive substance through said dispensing end;

an exterior actuation assembly operatively associated with said containment housing and structured to actuate said plunger assembly;

said containment housing further including an outlet defined therein and structured to permit passage of the radioactive substance out of said containment housing from said dispensing end of said syringe, for subsequent administering to the patient;

a secondary shielding assembly, said secondary shielding assembly being operatively associated with said outlet of said containment housing and structured to permit passage of the radioactive substance to the patient, said secondary shielding assembly at least partially formed from a radioactivity attenuating material disposed in protective, shielding relation to a portion of said containment housing so as to attenuate radioactivity emerging from said outlet.

2. A radioactive substance administrator as recited in claim 1 wherein said secondary shielding assembly includes a base structured to be disposed on an underlying support structure.

3. A radioactive substance administrator as recited in claim 1 wherein said secondary shielding assembly includes a main shielding body at least partially formed of radioactivity attenuating material disposed in substantially surrounding relation to said outlet so as to attenuate radioactivity emerging from said outlet and from the radioactive substance exiting said containment housing.

4. A radioactive substance administrator as recited in claim 3 further comprising a connector hub disposed in fluid flow communication with said dispensing end of said syringe, an irrigation source and the patient such that the radioactive substance emerging from said dispensing end of said syringe is directed into the patient by an irrigation fluid from said irrigation source.

5. A radioactive substance administrator as recited in claim 4 wherein said connector hub is at least partially shielded within said secondary shielding assembly so as to attenuate the emergence of radioactivity therefrom upon the radioactive substance being pushed into at least a vicinity of said connector hub for subsequent passage into the patient.

6. A radioactive substance administrator as recited in claim 5 wherein said irrigation source is disposed exterior of said secondary shielding assembly and is connected in said fluid flow communication with said connection hub by an elongate irrigation conduit.

7. A radioactive substance administrator as recited in claim 6 wherein said connection hub is connected to the patient by an elongate administration conduit.

8. A radioactive substance administrator as recited in claim 7 wherein said secondary shielding assembly includes at least two apertures defined therein and structured to permit the passage of said administration conduit and said irrigation conduit.

9. A radioactive substance administrator as recited in claim 3 wherein said main shielding body of said secondary shielding assembly includes an interior chamber formed of radioactivity attenuating material and structured to securely and at least partially retain said containment housing such that said outlet of said containment housing is substantially within said interior chamber during the urged passage of the radioactive substance out through said outlet of said containment housing from said dispensing end of said syringe, and such that the radioactivity emerging from the radioactive substance is at least temporarily attenuated.

10. A radioactive substance administrator as recited in claim 9 wherein said secondary shielding assembly is structured to clampingly receive said containment housing secured at least partially therein.

11. A radioactive substance administrator as recited in claim 3 wherein said containment housing includes a substantially non-malleable, rigid exterior layer structured to ensure that said containment housing substantially retains its shape and maintains a substantially precise engagement with said secondary shielding assembly subsequent to repeated uses.

12. A radioactive substance administrator as recited in claim 3 wherein said containment housing includes a retention portion and a track portion operatively and removably coupled with one another so as to removably enclose said syringe; said retention portion structured to contain a main body of said syringe and said track portion structured to contain said plunger track.

13. A radioactive substance administrator as recited in claim 3 wherein said containment housing is removably coupled to said secondary shielding assembly so as to permit introduction of said syringe into said containment housing at a shielded location remote from said secondary shielding assembly and the patient.

14. A radioactive substance administrator as recited in claim 3 wherein said containment housing includes a plunger port defined therein and structured to permit exterior access by said exterior actuation assembly to said plunger assembly of said syringe.

15. A radioactive substance administrator as recited in claim 14 wherein said exterior actuation assembly includes an elongate segment structured to extend through said plunger port into pushing engagement with said plunger assembly.

16. A radioactive substance administrator as recited in claim 15 wherein said exterior actuation assembly includes stopper assembly coupled to said elongate segment, said stopper assembly structured to attenuate radioactivity emerging from said containment housing through said plunger port.

17. A radioactive substance administrator as recited in claim 16 wherein said elongate segment includes an actuation end and a safety end, said stopper assembly being disposed relative to said elongate segment so as to at least partially define said actuation end and said safety end.

18. A radioactive substance administrator as recited in claim 17 wherein said actuation end is generally elongate so as to extend into actuating engagement with said plunger assembly and so as to urge said plunger assembly through said plunger track.

19. A radioactive substance administrator as recited in claim 18 wherein said safety end is structured to extend through said plunger port without actuating said plunger assembly and to generally abut said stopper assembly with said containment housing so as to substantially attenuate the emergence of radioactivity through said plunger port during transport and manipulation of said containment housing.

20. To administer a radioactive substance to a patient, a radioactive substance administrator comprising:

a syringe structured to receive a dosage of the radioactive substance therein;

said syringe including a dispensing end from which the radioactive substance exits said syringe, and a plunger assembly structured to urge the radioactive substance through said dispensing end;

a containment housing structured to substantially and removably contain said syringe, said containment housing including at least a radioactivity retard ant material layer disposed in substantially enclosing relation about said syringe and structured to substantially attenuate the emergence of radioactivity through said containment housing;

said containment housing including a plunger track defined therein and structured to contain said plunger assembly of said syringe, while also permitting movement of the plunger assembly so as to at least partially urge the radioactive substance through said dispensing end;

an exterior actuation assembly operatively associated with said containment housing and structured to actuate said plunger assembly;

said containment housing further including an outlet defined therein and structured to permit passage of the radioactive substance out of said containment housing from said dispensing end of said syringe, for subsequent administering to the patient;

a secondary shielding assembly, said secondary shielding assembly being operatively associated with said outlet of said containment housing and structured to permit passage of the radioactive substance to the patient, and to attenuate radioactivity emerging from said outlet of said containment housing and radioactivity from the radioactive substance exiting said containment housing, said secondary shielding assembly including a base structured to be disposed on an underlying support structure, said secondary shielding assembly including a main shielding body in which said containment housing is at least partially retained; and said main shielding body pivotally coupled to said base so as to facilitate horizontal introduction of said containment housing into said main shielding body, and subsequent vertical orientation of said containment housing so as to facilitate actuation of said exterior actuation assembly.

21. A radioactive substance administrator as recited in claim 20 wherein said base is structured to at least partially attenuate radioactivity and said main shielding body is structured to pivot into substantially closely spaced relation therewith so as to further attenuate the emergence of the radioactivity.

22. To administer a radioactive substance to a patient, a radioactive substance administrator comprising:

a syringe structured to receive a dosage of the radioactive substance therein;

said syringe including a dispensing end from which the radioactive substance exits said syringe, and a plunger assembly structured to urge the radioactive substance through said dispensing end;

a containment housing structured to substantially and removably contain said syringe, said containment housing including at least a radioactivity retardant material layer disposed in substantially enclosing relation about said syringe and structured to substantially attenuate the emergence of radioactivity through said containment housing;

said containment housing including a plunger track defined therein and structured to contain said plunger assembly of said syringe, while also permitting movement of the plunger assembly so as to at least partially urge the radioactive substance through said dispensing end;

an exterior actuation assembly operatively associated with said containment housing and structured to actuate said plunger assembly;

said containment housing further including an outlet defined therein and structured to permit passage of the radioactive substance out of said containment housing from said dispensing end of said syringe, for subsequent administering to the patient; and a secondary shielding assembly including a main shielding body and a base;

said main shielding body pivotally coupled to said base so as to facilitate horizontal introduction of said containment housing into said main shielding body and subsequent vertical orientation of said exterior actuation assembly.

23. A radioactive substance administrator as recited in claim 22 wherein said containment housing includes a retention portion and a track portion operatively and removably coupled with one another so as to removably enclose said syringe, said retention portion structured to contain a main body of said syringe and said track portion structured to contain said plunger track.

24. A radioactive substance administrator as recited in claim 22 wherein said containment housing includes a substantially non-malleable, rigid exterior layer disposed about said radioactivity retardant material layer and structured to ensure that said containment housing substantially retains its shape and maintains a substantially precise engagement with said secondary shielding assembly subsequent to repeated uses.

25. A radioactive substance administrator as recited in claim 22 wherein said containment housing includes a plunger port defined therein and structured to permit exterior access by said exterior actuation assembly to said plunger assembly of said syringe.

26. A radioactive substance administrator as recited in claim 25 wherein said exterior actuation assembly comprises:
   an elongate segment structured to extend through said plunger port into pushing engagement with said plunger assembly; and
   a stopper assembly coupled to said elongate segment, said stopper assembly structured to attenuate radioactivity emerging from said containment housing through said plunger port.

27. A radioactive substance administrator as recited in claim 26 wherein said elongate segment includes an actuation end and a safety end, said stopper assembly being disposed relative to said elongate segment so as to at least partially define said actuation end and said safety end.

28. A radioactive substance administrator as recited in claim 27 wherein said actuation end is generally elongate so as to extend into actuating engagement with said plunger assembly and so as to urge said plunger assembly through said plunger track; and
   said safety end is structured to extend through said plunger port without actuating said plunger assembly as so as to generally abut said stopper assembly with said containment housing so as to substantially attenuate the emergence of radioactivity through said plunger port during transport and manipulation of said containment housing.

* * * * *